United States Patent [19]

Yoshida et al.

[11] Patent Number: 5,264,637
[45] Date of Patent: Nov. 23, 1993

[54] PROCESS FOR PREPARING FLUOROALCOHOL

[75] Inventors: Tutomu Yoshida, Ibaraki; Kunitada Tanaka, Osaka; Yasumichi Chiba, Settsu; Yasuhisa Furutaka, Takatsuki; Yukio Homoto, Katano, all of Japan

[73] Assignee: Daikin Industries, Ltd., Osaka, Japan

[21] Appl. No.: 770,751

[22] Filed: Oct. 4, 1991

Related U.S. Application Data

[63] Continuation of Ser. No. 439,908, Nov. 29, 1989, abandoned.

[30] Foreign Application Priority Data

Nov. 24, 1988 [JP] Japan .............................. 63-297000
Nov. 25, 1988 [JP] Japan .............................. 63-298818

[51] Int. Cl.$^5$ ...................... C07C 31/38; C07C 29/124
[52] U.S. Cl. ......................................................... 568/842
[58] Field of Search ............................................ 568/842

[56] References Cited

FOREIGN PATENT DOCUMENTS 3016571 11/1981 Fed. Rep. of Germany ...... 568/842
1-199923 8/1989 Japan ................................... 568/842

OTHER PUBLICATIONS

Starks et al, Phase Transfer Catalysis, Academic Press New York, 1978, pp. 355, 67.
Dehmlow et al, Phase transfer catalysis, Verlag Chemie, Deerfield Beach, Florida (1980) p. 53.

Primary Examiner—Howard T. Mars
Attorney, Agent, or Firm—Nikaido, Marmelstein, Murray & Oram

[57] ABSTRACT

A fluoroalcohol of the formula $$Rf(CH_2CH_2OH)_n \qquad (1)$$

is prepared by the following three kinds of processes:
(a) by contacting a betaine compound with a halide compound of the formula $$Rf(CH_2CH_2X)_n \qquad (2)$$

to obtain an intermediate compound and subjecting the intermediate compound to hydrolysis,
(b) by contacting a betaine compound and water in the presence of an organic solvent with a halide compound of the formula $$Rf(CH_2CH_2X)_n \qquad (2), or$$

(c) by contacting a betaine type surfactant and water with a halide compound of the formula $$Rf(CH_2CH_2X)_n \qquad (2),$$

wherein Rf is $C_{2\sim13}$ fluoroalkyl or $C_{2\sim13}$ fluoroalkylene group, X is iodine or bromine, n is 1 when Rf is fluoroalkyl group and n is 2 when Rf is fluoroalkylene group.

7 Claims, No Drawings

PROCESS FOR PREPARING FLUOROALCOHOL

This application is a continuation of application Ser. No. 439,908, filed Nov. 29, 1989 now abandoned.

The present invention relates to processes for preparing a fluoroalcohol.

Fluoroalcohols are useful as an intermediate for water and oil repellent agent, surfactant, releasing agent or the like.

As processes for preparing a fluoroalcohol, the following methods are conventionally known.

① A method of contacting a starting fluoroalkyl iodide or bromide compound with fuming sulfuric acid or chlorosulfuric acid to prepare a sulfate and subsequently subjecting the sulfate to hydrolysis (JP-B-40-19085 and JP-B-58-39135), ② A method of contacting the same starting compound as above with dimethyl formamide and water (JP-B-52-8807), ③ A method of subjecting the same starting compound to hydrolysis in an aqueous solution of a nonoxidative oxyacid or hydrogen iodide at a pH of up to 2 (DE 2318677 A), ④ A method of contacting the same starting compound with water in an organic solvent in the presence of a heavy metal ion catalyst (JP-A-63-22040), etc.

However, in the method ①, fuming sulfuric acid and chlorosulfuric acid are strong in corrosion activity and a lot of by-products are formed such as dialkylsulfates and chlorides which are hardly subjected to hydrolysis. The method ② forms dimethylamine and formic acid as by-products, hence problem in recovery thereof. Further, a lot of compounds having terminal double bond are formed. In the method ③, it is difficult to choose a material durable to HI at a strong acidity of up to pH 2, at high temperature more than 200° C. and at high pressure. The method ④ has problems in toxicity of heavy metal, pollution derived therefrom and recovery of the metal.

An object of the present invention is to provide a process for preparing a fluoroalcohol which is safe and high in yield without use of dangerous chemicals and heavy metals.

The above and other objects of the invention will become apparent from the following description.

The present invention provides a process for preparing a fluoroalcohol of the formula $$Rf(CH_2CH_2OH)_n \qquad (1)$$

which comprises contacting a betaine compound with a halide compound of the formula $$Rf(CH_2CH_2X)_n \qquad (2)$$

to obtain an intermediate compound and subjecting the intermediate compound to hydrolysis, wherein Rf is $C_{2\sim13}$ fluoroalkyl or $C_{2\sim13}$ fluoroalkylene group, X is iodine or bromine, n is 1 when Rf is fluoroalkyl group and n is 2 when Rf is fluoroalkylene group.

This method is two-step reaction which comprises a first step of obtaining the intermediate in the absence of water and a second step of hydrolysis in the presence of an aqueous solution of alkali.

The starting compound of the present invention is a halide compound of the formula $$Rf(CH_2CH_2X)_n \qquad (2)$$

wherein Rf is $C_{2\sim13}$ fluoroalkyl or $C_{2\sim13}$ fluoroalkylene group, X is iodine or bromine, n is 1 when Rf is fluoroalkyl group and n is 2 when Rf is fluoroalkylene group.

Examples of useful halide compounds are $CF_3(CF_2)_7CH_2CH_2I$, $CF_3(CF_2)_9CH_2CH_2I$, $(CF_3)_2CF(CF_2)_4CH_2CH_2I$, $ICH_2CH_2(CF_2CF_2)_2CH_2CH_2I$, $ICH_2CH_2(CF_2CF_2)_3CH_2CH_2I$, $CF_3(CF_2)_7CH_2CH_2Br$, $CF_3(CF_2)_9CH_2CH_2Br$, $(CF_3)_2CF(CF_2)_4CH_2CH_2Br$, $BrCH_2CH_2(CF_2CF_2)_2CH_2CH_2Br$ and $BrCH_2CH_2(CF_2CF_2)_3CH_2CH_2Br$. The methods of preparing these compounds are disclosed in Journal of the Chemical Society, 3041 (1950), in the Journal of Organic Chemistry 23 1166 (1958), etc.

Preferable examples of betaine compounds used in the above method are those having the formula $$R^1R^2R^3N^{\oplus}CH_2CO_2^{\ominus} \qquad (3)$$

wherein $R^1$ and $R^2$ are each $C_{1\sim5}$ alkyl group, $R^3$ is $C_{1\sim24}$ alkyl group, and a hydrate of the compound. Examples thereof are $(CH_3)_3N^{\oplus}CH_2CO_2^{\ominus}$, $(CH_3)_3N^{\oplus}CH_2CO_2^{\ominus}.H_2O$, $(C_2H_5)_3N^{\oplus}CH_2CO_2^{\ominus}$, $C_8H_{17}(CH_3)_2N^{\oplus}CH_2CO_2^{\ominus}$, $C_{12}H_{25}(CH_3)_2N^{\oplus}CH_2CO_2^{\ominus}$ and $C_{18}H_{37}(CH_3)_2N^{\oplus}CH_2CO_2^{\ominus}$.

These betaine compounds are prepared by methods disclosed for example in U.S. Pat. No. 2,800,502, etc.

In the above method, when the halide compound (2) is contacted with the betaine compound (3), it is considered an intermediate compound having the following formula (4) is produced but the structure thereof is not confirmed.

$$Rf(CH_2CH_2OCOCH_2N^{\oplus}\!-\!R^1R^2R^3X^{\ominus})_n \qquad (4)$$

wherein Rf, $R^1$, $R^2$, $R^3$, X and n are same as above.

In the above method, the betaine compound (3) is used in an amount of usually 0.8 to 3.0 equivalents, preferably 1.2 to 1.5 equivalents per equivalent of the starting halide compound (one mole of the halide compound corresponds to one equivalent when n is 1 and two equivalents when n is 2). Further, an organic solvent is usually used in the reaction. Examples thereof are 1-butanol, 2-butanol. 2-methyl-2-propanol, toluene, xylene, sulfolane, N-methylpyrrolidone, γ-butyrolactone and propionic acid. Alcohol is preferably used because high selectivity is obtained. The reaction temperature is usually 80° to 250° C. and preferably 100° to 150° C. in view of high reaction velocity, easy heating procedure and easy selection of solvent.

The hydrolysis of the above intermediate compound is conducted by addition of an aqueous solution of an alkali to the reaction mixture. The kind of alkali is not particularly limited but usually sodium hydroxide or potassium hydroxide is used. The alkali is used in an amount of usually at least one equivalent, preferably 1.2 to 5 equivalents per equivalent of the halide compound (2). The alkali is usually 5 to 15% by weight in concentration. The reaction temperature is usually 0° to 80° C., preferably 20° to 40° C. By hydrolysis of the intermediate compound, the desired fluoroalcohol of the following formula (1) can be obtained, $$Rf(CH_2CH_2OH)_n \qquad (1)$$

wherein Rf and n are same as above.

As a second embodiment, the present invention provides a process for preparing a fluoroalcohol of the formula $$Rf(CH_2CH_2OH)_n \qquad (1)$$

which is a single-step process and comprises contacting a betaine compound and water in the presence of an organic solvent with a halide compound of the formula $$Rf(CH_2CH_2X)_n \qquad (2)$$

wherein Rf, X and n are same as above.

Preferable examples of betaine compounds used in the above method are those having the formula $$R^4R^5R^6N^{\oplus}CH_2CO_2^{\ominus} \qquad (5)$$

wherein $R^4$, $R^5$ and $R^6$ are each $C_{1\sim24}$ alkyl group. Examples thereof are $(CH_3)_3N^{\oplus}CH_2CO_2^{\ominus}$, $(C_2H_5)_3N^{\oplus}CH_2CO_2^{\ominus}$, $C_8H_{17}(CH_3)_2N^{\oplus}CH_2CO_2^{\ominus}$, $C_{12}H_{25}(CH_3)_2N^{\oplus}CH_2CO_2^{\ominus}$ and $C_{18}H_{37}(CH_3)_2N^{\oplus}CH_2CO_2^{\ominus}$. These betaine compounds are prepared by methods disclosed for example in U.S. Pat. No. 2,800,502, etc.

The organic solvent used in the above method is preferably soluble with water and promotes a mixing of the starting halide compound and water. Examples of useful organic solvents are methanol, ethanol, propanol or like alcohols, acetone, acetonitrile, ethylene glycol, glycerin, glyme, cellosolve, propionic acid, phenol, cresol, sulfolane, N-methylpyrrolidone, γ-butyrolactone, etc.

In the above method, the betaine compound (5) is used in an amount of usually 1 to 20 equivalents, preferably 1.2 to 5 equivalents per equivalent of the starting halide compound. Further, water is used in an amount of usually 1 to 200 equivalents, preferably 2 to 140 equivalents per equivalent of the starting halide compound, one mole of water being two equivalents. The organic solvent is used in an amount of 0.1 to 10 parts by volume, preferably 1 to 5 parts by volume per parts by volume of water. The reaction temperature is usually 80° to 200° C. and preferably 120° to 160° C. in view of high reaction velocity and easy heating procedure. The reaction time is usually sufficient in 1 to 10 hours and preferably 2 to 6 hours.

Further, as a third embodiment, the present invention provides a process for preparing a fluoroalcohol of the formula $$Rf(CH_2CH_2OH)_n \qquad (1)$$

which is a single-step process and comprises contacting a betaine type surfactant and water with a halide compound of the formula $$Rf(CH_2CH_2X)_n \qquad (2)$$

wherein Rf, X and n are same as above. It is possible, in this method, to omit an organic solvent by using the betaine type surfactant.

Preferable examples of betaine type surfactants used in the above method are those having the formula $$R^7R^8R^9N^{\oplus}CH_2CO_2^{\ominus} \qquad (6)$$

wherein $R^7$ and $R^8$ are each $C_{1\sim5}$ alkyl group and $R^9$ is $C_{6\sim24}$, preferably $C_{8\sim20}$ alkyl group. Examples thereof are $C_8H_{17}(CH_3)_2N^{\oplus}CH_2CO_2^{\ominus}$, $C_{12}H_{25}(CH_3)_2N^{\oplus}CH_2CO_2^{\ominus}$ and $C_{18}H_{37}(CH_3)_2N^{\oplus}CH_2CO_2^{\ominus}$.

Further, in the above method, it is possible, as required, to replace a part or most of the above betaine type surfactant by a betaine compound of the formula $$R^{10}R^{11}R^{12}N^{\oplus}CH_2CO_2^{\ominus} \qquad (7)$$

wherein $R^{10}$, $R^{11}$ and $R^{12}$ are each $C_{1\sim5}$ alkyl group. These betaine type surfactants and other betaine compounds are prepared by methods disclosed for example in U.S. Pat. No. 2,800,502, etc.

In the above method, the betaine type surfactant is used in an amount of usually 1 to 20 equivalents, preferably 1.2 to 5 equivalents per equivalent of the starting halide compound. When the betain type surfactant is replaced by other betain compound, the betaine type surfactant is used preferably in an amount of at least 0.2 equivalent. Further, water is used in an amount of usually 1 to 200 equivalents, preferably 2 to 140 equivalents per equivalent of the starting halide compound, one mole of water being two equivalents. The reaction temperature is usually 80° to 200° C. and preferably 120° to 160° C. in view of high reaction velocity and easy heating procedure. The reaction time is usually sufficient in 1 to 10 hours and preferably 2 to 6 hours. In the above method, since the halide compound is contacted with a betaine type surfactant, an organic solvent needs not to be used.

The desired compound of the invention can be separated and purified by known methods, for example, by extraction, distillation, recrystallization, gas chromatography and column chromatography.

The present processes are safe without use of dangerous chemicals and heavy metals. Further, in the present processes, conversion of the starting compound and selectivity of the desired compound are excellent.

The present invention is described by showing examples below.

EXAMPLE 1

Into a 50-ml four-necked flask equipped with a stirrer, condenser and thermometer were placed 5.0 g of $C_8F_{17}CH_2CH_2I$, 3.1 g of $(CH_3)_3N^{\oplus}CH_2COO^{\ominus}$ and 10 ml of 1-butanol and the mixture was reacted with stirring at 130° to 135° C. for 3 hours.

Subsequently to the mixture were added 10 ml of 3N-aqueous solution of potassium hydroxide and 10 ml of trichlorotrifluoroethane with stirring.

Analysis of a lower layer by gas chromatography showed $C_8F_{17}CH_2CH_2OH$ was obtained in 93% selectivity with 100% conversion of $C_8F_{17}CH_2CH_2I$.

EXAMPLE 2

Into a same flask as in Example 1 were placed 5.0 g of $C_8F_{17}CH_2CH_2I$, 3.0 g of $(CH_3)_3N^{\oplus}CH_2COO^{\ominus}$ and 10 ml of 2-butanol and the mixture was reacted with stirring at 110° C. for 4 hours.

Subsequently to the mixture were added 10 ml of 3N-aqueous solution of potassium hydroxide and 10 ml of trichlorotrifluoroethane with stirring.

Analysis of a lower layer by gas chromatography showed $C_8F_{17}CH_2CH_2OH$ was obtained in 92% selectivity with 100% conversion of $C_8F_{17}CH_2CH_2I$.

EXAMPLE 3

Into a same flask as in Example 1 were placed 5.0 g of $C_8F_{17}CH_2CH_2I$, 3.0 g of $(CH_3)_3N^{\oplus}CH_2COO^{\ominus}$ and 10 ml of 2-butanol and the mixture was reacted with stirring at 100° to 105° C. for 5 hours.

Subsequently to the mixture were added 10 ml of 3N-aqueous solution of potassium hydroxide and 10 ml of trichlorotrifluoroethane with stirring.

Analysis of a lower layer by gas chromatography showed $C_8F_{17}CH_2CH_2OH$ was obtained in 90% selectivity with 87% conversion of $C_8F_{17}CH_2CH_2I$.

EXAMPLE 4

Into a 100-ml four-necked flask equipped with a stirrer, condenser and thermometer were placed 10.0 g of $ICH_2CH_2(CF_2)_6CH_2CH_2I$, 4.6 g of $(CH_3)_3N^{\oplus}CH_2COO^{\ominus}$ and 10 ml of 2-butanol and the mixture was reacted with stirring at 105° to 108° C. for 4.5 hours.

Subsequently to the mixture were added 20 ml of 3N-aqueous solution of potassium hydroxide and 20 ml of ethyl acetate with stirring.

Analysis of an upper layer by gas chromatography showed $HOCH_2CH_2(CF_2)_6CH_2CH_2OH$ was obtained in 85% selectivity with 99% conversion of $ICH_2CH_2(CF_2)_6CH_2CH_2I$ and 10% of $CH_2=CH(CF_2)_6CH_2CH_2OH$ was formed as a by-product.

EXAMPLE 5

Into a 100-ml four-necked flask equipped with a stirrer, condenser and thermometer were placed 10.0 g of $C_8F_{17}CH_2CH_2I$, 8.0 g of $C_{12}H_{25}(CH_3)_2N^{\oplus}CH_2COO^{\ominus} \cdot H_2O$ and 30 ml of 1-butanol and the mixture was reacted with stirring at 105° to 108° C. For 5 hours.

Subsequently to the mixture were added 20 ml of 3N-aqueous solution of potassium hydroxide, 20 ml of ethyl acetate and 2 g of sodium chloride with stirring.

Analysis of an upper layer by gas chromatography showed $C_8F_{17}CH_2CH_2OH$ was obtained in 87% selectivity with 87% conversion of $C_8F_{17}CH_2CH_2I$.

EXAMPLE 6

Into a 200-ml autoclave were placed 57.4 g (100 mmol) of $CF_3(CF_2)_7CH_2CH_2I$, 14.1 g (120 mmol) of $(CH_3)_3N^{\oplus}CH_2COO^{\ominus}$, 50 g of isopropanol (IPA) and 20 g of water, and the mixture was stirred at 150° C. for 6 hours. After cooled to room temperature, the reaction mixture was extracted with each 100 ml of water and trichlorotrifluoroethane (R-113). Analysis of an oil layer by gas chromatography showed $CF_3(CF_2)_7CH_2CH_2OH$ was obtained in 97% conversion and 93% selectivity.

EXAMPLE 7

Into a 200-ml autoclave were placed 61.0 g (100 mmol) of $ICH_2CH_2(CF_2)_6CH_2CH_2I$, 28.1 g (240 mmol) of $(CH_3)_3N^{\oplus}CH_2COO^{\ominus}$, 60 g of IPA and 30 g of water, and the mixture was stirred at 150° C. for 6 hours. After cooled to room temperature, the reaction mixture was extracted with each 100 ml of water and R-113. Analysis of an oil layer by gas chromatography showed $HOCH_2CH_2(CF_2)_6CH_2CH_2OH$ was obtained in 87% selectivity. Conversion of $ICH_2CH_2(CF_2)_6CH_2CH_2I$ was 95% and 10% of $CH_2=CH(CF_2)_6CH_2CH_2OH$ was formed as a by-product.

EXAMPLE 8

Into a 200-ml autoclave were placed 57.4 g (100 mmol) of $CF_3(CF_2)_7CH_2CH_2I$, 11.7 g (100 mmol) of $(CH_3)_3N^{\oplus}CH_2COO^{\ominus}$, 40 g of IPA, 15 g of water and 5.4 g (20 mmol) of $C_{12}H_{25}(CH_3)_2N^{\oplus}CH_2COO^{\ominus}$ as a betaine type surfactant, and the mixture was stirred at 150° C. for 6 hours. After cooled to room temperature, the reaction mixture was extracted with each 100 ml of water and R-113. Analysis of an oil layer by gas chromatography showed $CF_3(CF_2)_7CH_2CH_2OH$ was obtained in 99% conversion and 95% selectivity.

EXAMPLES 9 TO 12

The reactions were conducted in the same manner as in Example 6 except that solvents listed in Table 1 were used in place of isopropanol. Table 1 also shows conversion of $CF_3(CF_2)_7CH_2CH_2I$ and selectivity of $CF_3(CF_2)_7CH_2CH_2OH$.

TABLE 1

| Ex. | Organic solvent | Conv. | Selec. |
|---|---|---|---|
| 9 | m-cresol | 92% | 98% |
| 10 | ethanol | 100% | 95% |
| 11 | methanol | 97% | 88% |
| 12 | acetonitrile | 96% | 92% |

COMPARISON EXAMPLE 1

The reaction was conducted in the same manner as in Example 6 except that the betaine compound of Example 6 was not used. Conversion of $CF_3(CF_2)_7CH_2CH_2I$ was 0%.

EXAMPLE 13

Into a 200-ml autoclave were placed 57.4 g (100 mmol) of $CF_3(CF_2)_7CH_2CH_2I$, 100 g of water and 32.6 g (120 mmol) of $C_{12}H_{25}(CH_3)_2N^{\oplus}CH_2COO^{\ominus}$ as a betaine type surfactant, and the mixture was stirred at 150° C. for 6 hours. After cooled to room temperature, the reaction mixture was extracted with each 100 ml of water and R-113. Analysis of an oil layer by gas chromatography showed $CF_3(CF_2)_7CH_2CH_2OH$ was obtained in 99% conversion and 96% selectivity.

EXAMPLE 14

Into a 200-ml autoclave were placed 61.0 g (100 mmol) of $ICH_2CH_2(CF_2)_6CH_2CH_2I$, 100 g of water and 65.1 g (240 mmol) of $C_{12}H_{25}(CH_3)_2N^{\oplus}CH_2COO^{\ominus}$ as a betaine type surfactant, and the mixture was stirred at 150° C. for 6 hours. After cooled to room temperature, the reaction mixture was extracted with each 100 ml of water and R-113. Analysis of an oil layer by gas chromatography showed $HOCH_2CH_2(CF_2)_6CH_2CH_2OH$ was obtained in 90% selectivity. Conversion of $ICH_2CH_2(CF_2)_6CH_2CH_2I$ was 99% and 8% of $CH_2=CH(CF_2)_6CH_2CH_2OH$ was formed as a by-product.

EXAMPLE 15

Into a 200-ml autoclave were placed 43.1 g (75 mmol) of $CF_3(CF_2)_7CH_2CH_2I$, 8.8 g (75 mmol) of $(CH_3)_3N^{\oplus}CH_2COO^{\ominus}$, 60 g of water and 4.1 g (15 mmol) of $C_{12}H_{25}(CH_3)_2N^{\oplus}CH_2COO^{\ominus}$ as a betaine type surfactant, and the mixture was stirred at 150° C. for 6 hours. After cooled to room temperature, the reaction mixture was extracted with each 100 ml of water and R-113. Analysis of an oil layer by gas chromatography showed $CF_3(CF_2)_7CH_2CH_2OH$ was obtained in 99% conversion and 97% selectivity.

COMPARISON EXAMPLE 2

The reaction was conducted in the same manner as in Example 13 except that 32.8 g (120 mmol) of sodium laurylsulfate (anionic surfactant) was used in place of the betaine type surfactant of Example 13. Conversion of $CF_3(CF_2)_7CH_2CH_2I$ was 0%.

COMPARISON EXAMPLE 3

The reaction was conducted in the same manner as in Example 13 except that 41.8 g (120 mmol) of octadecyltrimethylammonium chloride (cationic surfactant) was used in place of the betaine type surfactant of Example 13. Conversion of $CF_3(CF_2)_7CH_2CH_2I$ was 0%.

COMPARISON EXAMPLE 4

The reaction was conducted in the same manner as in Example 13 except that

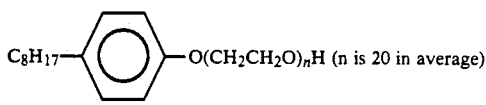

(nonionic surfactant) was used in place of the betaine type surfactant of Example 13. Conversion of $CF_3(CF_2)_7CH_2CH_2I$ was 0%.

We claim:

1. A process for preparing a fluoroalcohol of the formula $$Rf(CH_2CH_2OH)_n \qquad (1)$$

which comprises contacting a betaine compound, in the absence of water with a halide compound of the formula $$Rf(CH_2CH_2X)_n \qquad (2)$$

to obtain an intermediate compound, said betaine compound being used in an amount of 0.8 to 3.0 equivalents per equivalent of the halide compound, and subjecting the intermediate compound to hydrolysis with an alkali, wherein Rf is a $C_{2\sim13}$ perfluoroalkyl or a $C_{2\sim13}$ perfluoroalkylene group, X is iodine or bromine, n is 1 when Rf is a perfluoroalkyl group and n is 2 when Rf is a perfluoroalkylene group.

2. A process as defined in claim 1 wherein the betaine compound has the formula $$R^1R^2R^3N^{\oplus}CH_2CO_2^{\ominus} \qquad (3)$$

wherein $R^1$ and $R^2$ are each $C_{1\sim5}$ alkyl group, $R^3$ is $C_{1\sim24}$ alkyl group, and a hydrate of the compound.

3. A process for preparing a fluoroalcohol of the formula $$Rf(CH_2CH_2OH)_n \qquad (1)$$

which comprises contacting a betaine compound and water in the presence of a water soluble organic solvent with a halide compound of the formula $$Rf(CH_2CH_2X)_n \qquad (2)$$

said betaine compound being used in an amount of 1 to 20 equivalents per equivalent of the halide compound, wherein Rf is a $C_{2\sim13}$ perfluoroalkyl or a $C_{2\sim13}$ perfluoroalkylene, X is iodine or bromine and n is 1 when Rf is a perfluoroalkyl group and n is 2 when Rf is a perfluoroalkylene group.

4. A process as defined in claim 3 wherein the betaine compound has the formula $$R^4R^5R^6N^{\oplus}CH_2CO_2^{\ominus} \qquad (5)$$

wherein $R^4$, $R^5$ and $R^6$ are each $C_{1\sim24}$ alkyl group.

5. A process for preparing a fluoroalcohol of the formula $$Rf(CH_2CH_2OH)_n \qquad (1)$$

which comprises contacting a betaine compound, comprising a betaine type surfactant having one pendant alkyl group of 6 to 24 carbon atoms, and water in the absence of an organic solvent with a halide compound of the formula $$Rf(CH_2CH_2X)_n \qquad (2)$$

said betaine type surfactant being used in an amount of 1 to 20 equivalents per equivalent of the halide compound, wherein Rf is a $C_{2-13}$ perfluoroalkyl or a $C_{2-13}$ perfluoroalkylene, X is iodine or bromine and n is 1 when Rf is a perfluoroalkyl group and n is 2 when Rf is a perfluoroalkylene group.

6. A process as defined in claim 5 wherein the betaine type surfactant has the formula $$R^7R^8R^9N^{\oplus}CH_2CO_2^{\ominus} \qquad (6)$$

wherein $R^7$ and $R^8$ are each $C_{1\sim5}$ alkyl group and $R^9$ is $C_{6\sim24}$ alkyl group.

7. A process as defined in claim 6 wherein a part or most of the betaine type surfactant is replaced by a betaine compound of the formula $$R^{10}R^{11}R^{12}N^{\oplus}CH_2CO_2^{\ominus} \qquad (7)$$

wherein $R^{10}$, $R^{11}$ and $R^{12}$ are each $C_{1\sim5}$ alkyl group.

* * * * *